(12) United States Patent
Norwood

(10) Patent No.: US 9,918,626 B2
(45) Date of Patent: Mar. 20, 2018

(54) LARGE PATIENT HEAD AND CHIN REST

(71) Applicant: Rick A. Norwood, Blue Bell, PA (US)

(72) Inventor: Rick A. Norwood, Blue Bell, PA (US)

( * ) Notice: Subject to any disclaimer, the term of this patent is extended or adjusted under 35 U.S.C. 154(b) by 0 days.

(21) Appl. No.: 14/918,563

(22) Filed: Oct. 21, 2015

(65) Prior Publication Data
US 2016/0270650 A1 Sep. 22, 2016

Related U.S. Application Data

(60) Provisional application No. 62/136,338, filed on Mar. 20, 2015.

(51) Int. Cl.
*A61B 3/00* (2006.01)
*A61B 3/02* (2006.01)

(52) U.S. Cl.
CPC .................. *A61B 3/0083* (2013.01)

(58) Field of Classification Search
USPC ................................................ 351/200–246
See application file for complete search history.

(56) References Cited

U.S. PATENT DOCUMENTS

| 4,934,809 A * | 6/1990 | Volk ...................... A61B 3/135 351/205 |
| 2004/0004694 A1* | 1/2004 | Sugino .................... A61B 3/14 351/206 |
| 2006/0109424 A1* | 5/2006 | Nicolini ................. A61B 3/028 351/244 |

\* cited by examiner

*Primary Examiner* — Mohammed Hasan
(74) *Attorney, Agent, or Firm* — Ruben C. DeLeon

(57) ABSTRACT

An improved eye examination device for use of an eye examination is described herein. The device includes a support device enclosing a chin rest for an eye patient to place their chin in order for an eye professional/technician to examine at least one eye of the eye patient.

18 Claims, 7 Drawing Sheets

LARGE PATIENT HEAD AND CHIN REST

BRIEF DESCRIPTION OF THE FIGURES

For a more complete understanding of the present invention, including its features and advantages, reference is now made to the detailed description of the invention taken in conjunction with the accompanying drawing in which.

DETAILED DESCRIPTION OF THE INVENTION

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

An eye examination is a series of tests performed by an ophthalmologist (medical doctor), optometrist, or orthoptist assessing vision and ability to focus on and discern objects, as well as other tests and examinations pertaining to the eyes. Health care professionals often recommend that all people should have periodic and thorough eye examinations as part of routine primary care, especially since many eye diseases are asymptomatic.

Eye examinations may detect potentially treatable blinding eye diseases, ocular manifestations of systemic disease, or signs of tumours or other anomalies of the brain.

Ideally, the eye examination consists of an external examination, followed by specific tests for visual acuity, pupil function, extraocular muscle motility, visual fields, intraocular pressure and ophthalmoscopy through a dilated pupil.

A minimal eye examination consists of tests for visual acuity, pupil function, and extraocular muscle motility, as well as direct ophthalmoscopy through an undilated pupil.

Close inspection of the anterior eye structures and ocular adnexa are often done with a slit lamp which is a table mounted microscope with a special adjustable illumination source attached. A small beam of light that can be varied in width, height, incident angle, orientation and colour, is passed over the eye. Often, this light beam is narrowed into a vertical "slit", during slit-lamp examination. The examiner views the illuminated ocular structures, through an optical system that magnifies the image of the eye and the patient is seated while being examined, and the head stabilized by an adjustable chin rest.

This allows inspection of all the ocular media, from cornea to vitreous, plus magnified view of eyelids, and other external ocular related structures. Fluorescein staining before slit lamp examination may reveal corneal abrasions or herpes simplex infection.

The binocular slit-lamp examination provides stereoscopic magnified view of the eye structures in striking detail, enabling exact anatomical diagnoses to be made for a variety of eye conditions.

Also ophthalmoscopy and gonioscopy examinations can also be performed through the slit lamp when combined with special lenses. These lenses include the Goldmann 3-mirror lens, gonioscopy single-mirror/Zeiss 4-mirror lens for (ocular) anterior chamber angle structures and +90D lens, +78D lens, +66D lens & Hruby (−56D) lens, the examination of retinal structures is accomplished.

Intraocular pressure (TOP) can be measured by Tonometry devices. The eye can be thought of as an enclosed compartment through which there is a constant circulation of fluid that maintains its shape and internal pressure. Tonometry is a method of measuring this pressure using various instruments. The normal range is 10-21 mmHg.

Some of these types of eye examinations include placing the chin of a patient on a chin rest within a support device and then measuring the eye sight. However, most chin rests within standard support devices do not adequately support larger patients. Thus, this type of patient feels uncomfortable when the chin is placed on the chin rest of the device. For example, bigger patients have to squeeze their upper body into the support device in order to place their chin on the chin rest which can be very uncomfortable to the patient.

Therefore, a need exists for a chin rest within a support device that is comfortable for larger patients, as well medium sized patients, to place their chin on the chin rest for the eye examination. The present invention has an advantage to solve this need.

Figure 1:
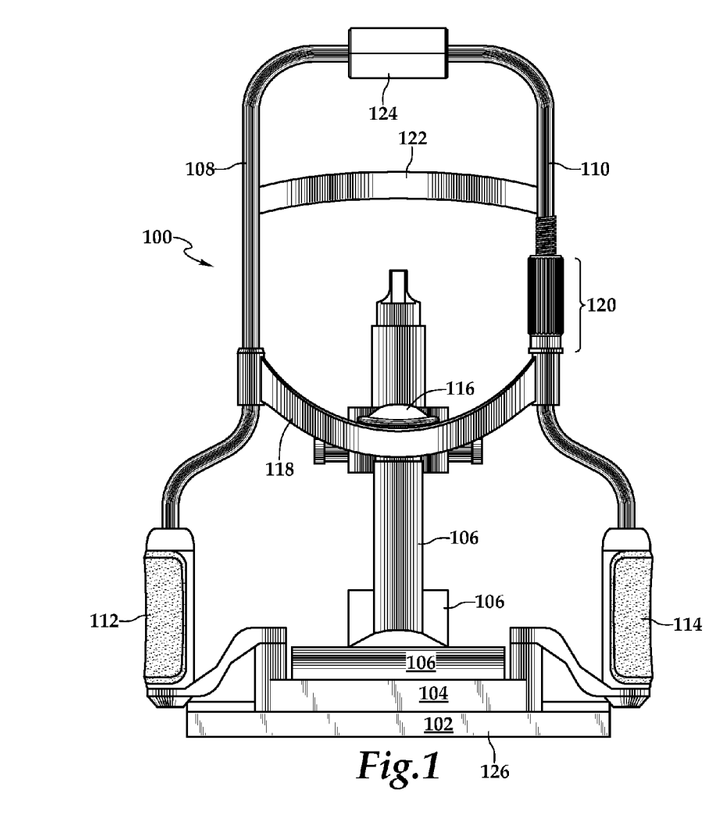
FIG. 1 illustrates a front view of an embodiment of present invention.

Now turning to FIG. 1, an embodiment of the present invention is illustrated. In this embodiment, a chin rest and head support system 100 is shown attached to table 102. In turn, a support level 104 is attached to the table 102 along with a medical eye testing device 106. The eye testing device 106 is positioned adjacent to the support system 100 in order to allow an eye professional/technician to exam a patient. The support system 100 includes a left support bar 108 as well as a right support bar 110. Also shown in this figure, is a left handle 112 near the bottom of the left support bar 108. Similarly, a right handle 114 near the bottom of the right support bar 110 is shown.

Also shown in this figure is a chin rest 116 attached near the center of curved chin bar 118. The curved chin bar 118 is attached to the right support bar 110 as well as the left support bar 108. At the juncture where the curved chin bar 118 is attached to the right support bar 108, a mechanism 120 allows the curved chin bar 118 to adjust vertically as may be required for the comfort of the patient to be examined. In addition, the head rest 122 is shown attached to the right support bar 110 as well as the left support bar 108. Moreover a handle 124 is shown that may be used to grip the support system 100 in order to reposition or move the support system 100.

Figure 2:
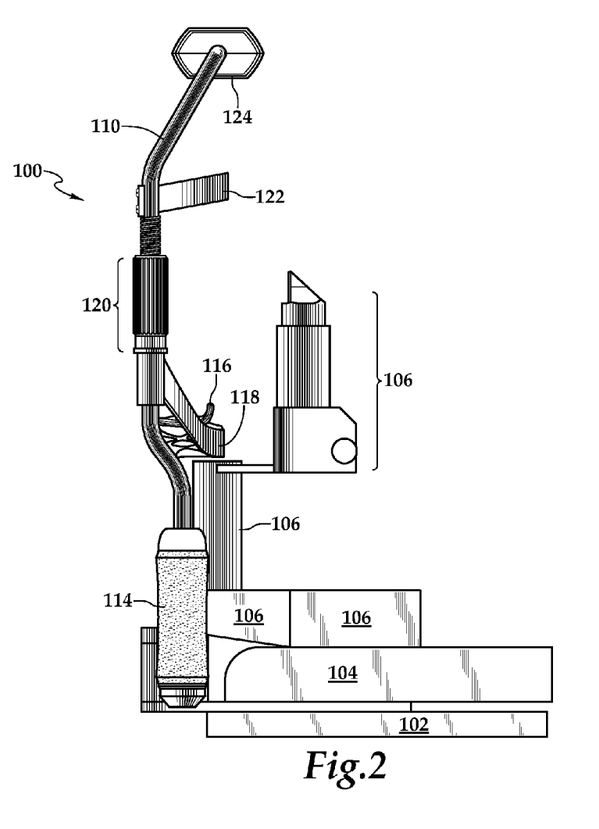
FIG. 2 illustrates a side view of this embodiment of the present invention.

FIG. 2 illustrates the support system 100 from a side view. In this figure, the grip 124 is shown attached to the right support bar 110 which includes the adjustment mechanism 120 and the right handle 114. In addition, the head rest 122, the chin rest 116 and curved chin bar 118 along with the eye testing device 106 and the support level 104 are shown.

Figure 3:
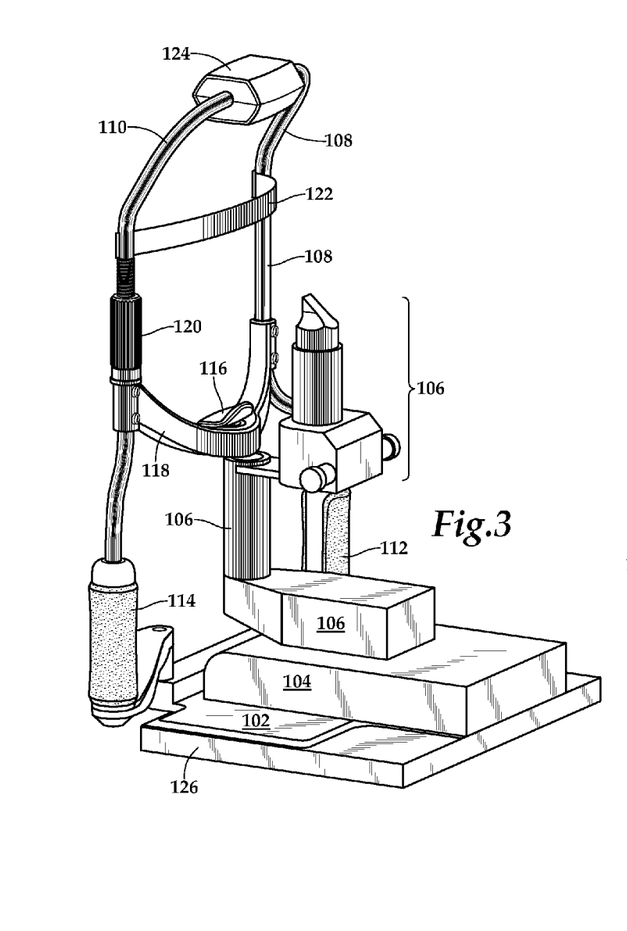
FIG. 3 is rear/side view of this embodiment of the present invention.

FIG. 3 illustrates a different perspective of the support system 100 from a rear/side view. In this figure, a chin rest and head support system 100 is shown attached to table 102, which in turn is on top of an additional table 126. However, in other embodiments, the table 102 and the additional table 126 can be combined as well as other configurations of similar supports can be utilized.

Moreover, a support level 104 is attached to the table 102 along with an eye testing device 106. Similar to FIG. 2, the eye testing device 106 is positioned adjacent to the support system 100 in order to allow an eye professional/technician to exam a patient. Additionally, the support system 100 includes the left support bar 108 as well as a right support bar 110. Also shown in this figure, is the left handle 112 near the bottom of the left support bar 108. Likewise, the right handle 114 near the bottom of the right support bar 110 is shown.

Also shown in this figure is the chin rest 116 attached near the center of the curved chin bar 118. The curved chin bar 118 is attached to the right support bar 110 as well as the left support bar 108. At the juncture where the curved chin bar 118 is attached to the right support bar 108, the adjustment mechanism 120 allows the curved chin bar 118 to adjust vertically as shown in FIG. 1. In addition, the head rest 122 is shown attached to the right support bar 110 as well as the left support bar 108. Moreover the handle 124 is shown that may be used to grip the support system 100 in order to reposition or move the support system 100.

Figure 4:
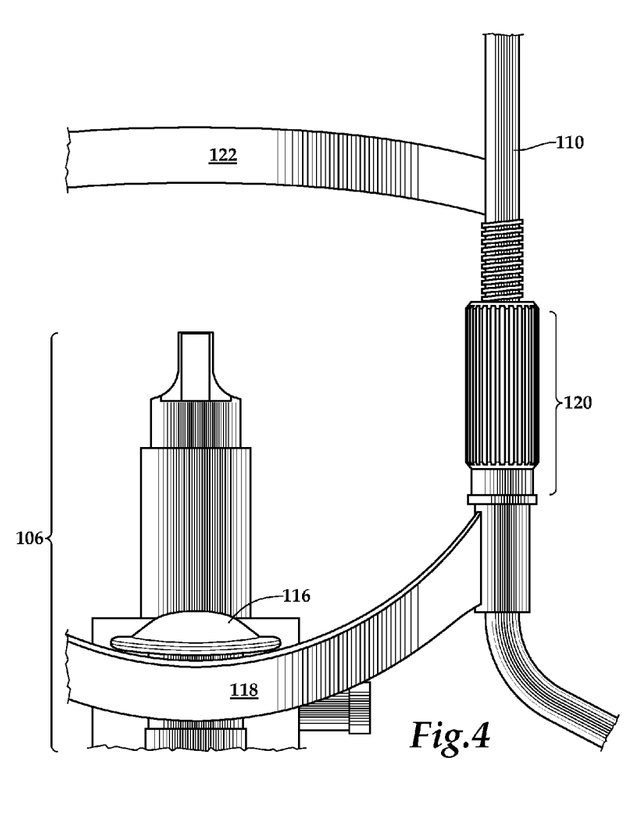
FIG. 4 is a detailed view of a portion of the present invention.

FIG. 4 illustrates a detailed view of the adjustment mechanism 120 that allows the chin rest 116 and the curved chin bar 118 vertically adjust as desired by the eye professional/technician and/or the patient. In this figure, the head rest 122, the right support bar 110, as well as the eye testing device 106 are shown.

Figure 5:
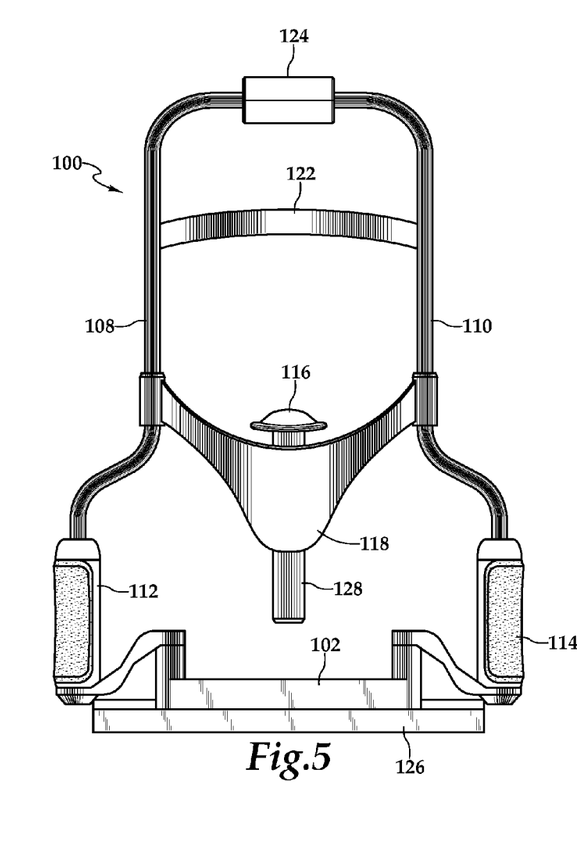
FIG. 5 illustrates a front view of another embodiment of present invention.

FIG. 5 illustrates another embodiment of the invention. Similar to the first embodiment, the support system 100 includes the left support bar 108, the right support bar 110, the curved chin bar 118, the chin rest 116, the left handle 112, the right handle 114, the head rest 122 and the handle 124. In this embodiment, similarly to FIG. 3, the support system 100 is shown attached to table 102, which in turn is on top of an additional table 126. However, in other embodiments, the table 102 and the additional table 126 can be combined as well as other configurations of similar supports can be utilized. In addition, this embodiment includes an adjustment bar 128 which elevates the chin rest 116 as desired by the eye professional/technician and/or the patient.

Figures 6, 7:
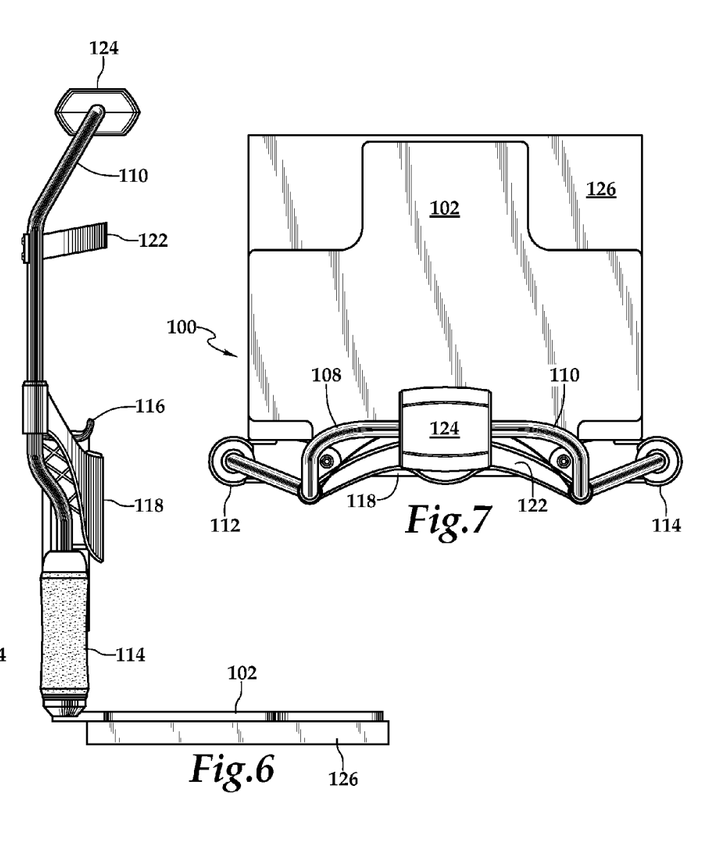
FIG. 6 illustrates a side view of this embodiment of the present invention.
FIG. 7 is top of this embodiment of the present invention.

FIG. 6 illustrates a side view of embodiment of FIG. 5. Similar to the first embodiment, the support system 100 includes the right support bar 110, the curved chin bar 118, the chin rest 116, the right handle 114, the head rest 122 and the handle 124. In this embodiment, similarly to FIG. 5, the support system 100 is shown attached to table 102, which in turn is on top of an additional table 126. Moreover, although not shown, this embodiment includes the adjustment bar 128 which elevates the chin rest 116 as desired by the eye professional/technician and/or the patient.

FIG. 7 illustrates a top view of embodiment of FIG. 5. This figure illustrates the support system 100 which includes the right support bar 110, the left support bar 112, the curved chin bar 118, the chin rest 116, the right handle 114, the left handle 112 the head rest 122 and the handle 124. Additionally, the support system 100 is shown attached to table 102, which in turn is on top of an additional table 126. Moreover, although not shown, this embodiment includes the adjustment bar 128 which elevates the chin rest 116 as desired by the eye professional/technician and/or the patient.

Figure 8:
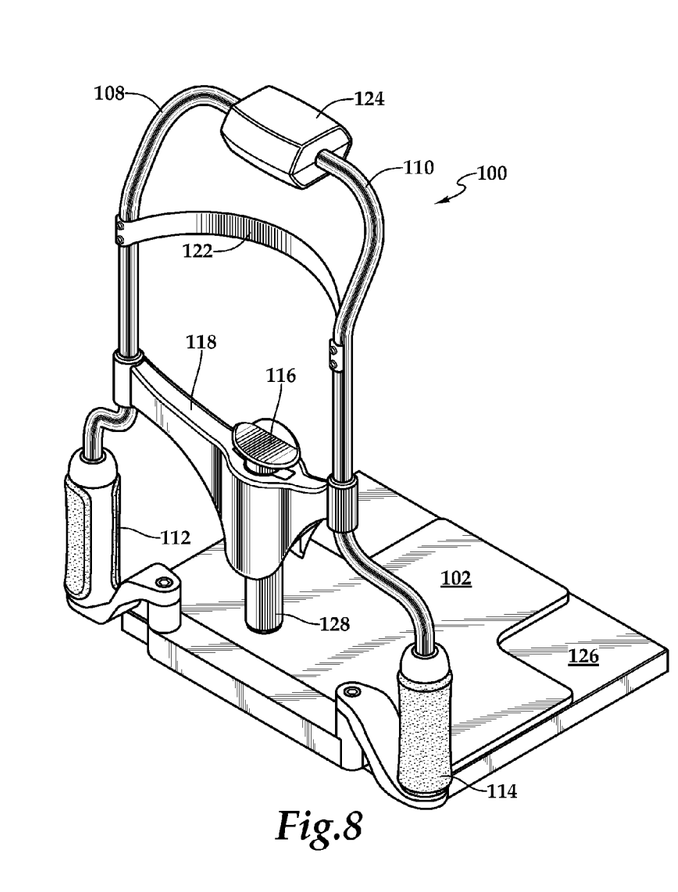
FIG. 8 is a top/front view of this embodiment of the present invention.

FIG. 8 illustrates another perspective of this embodiment from a top/front view. In this figure, the support system 100 includes the left support bar 108, the right support bar 110, the curved chin bar 118, the chin rest 116, the left handle 112, the right handle 114, the head rest 122 and the handle 124. Like FIG. 5, the support system 100 is shown attached to table 102, which in turn is on top of an additional table 126. However, in other embodiments, the table 102 and the additional table 126 can be combined as well as other configurations of similar supports can be utilized. In addition, this embodiment includes an adjustment bar 128 which elevates the chin rest 116 as desired by the eye professional/technician and/or the patient.

Figure 9:
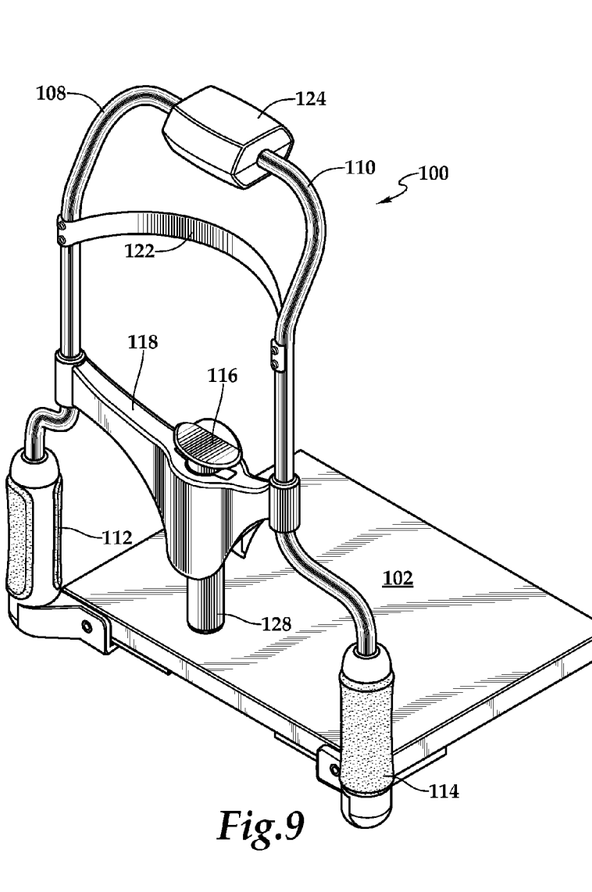
FIG. 9 is a top/front view of another embodiment of the present invention.

FIG. 9 illustrates a perspective of another embodiment of the present invention from a top/front view. In this figure, the support system 100 includes the left support bar 108, the right support bar 110, the curved chin bar 118, the chin rest 116, the left handle 112, the right handle 114, the head rest 122 and the handle 124. In this embodiment, the support system 100 is shown attached to table 102. However, this embodiment does include the adjustment bar 128 which elevates the chin rest 116 as desired by the eye professional/technician and/or the patient.

Figure 10:
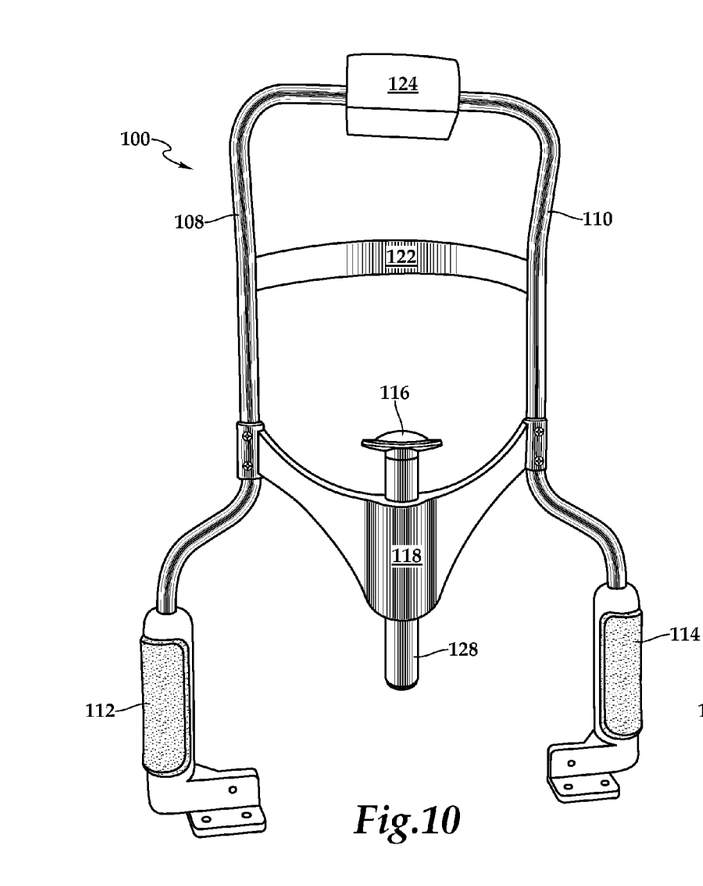
FIG. 10 illustrates a front view of another embodiment of present invention.

FIG. 10 illustrates a front view of an embodiment of the invention similar to the previously described embodiment. In this embodiment, the support system 100 includes the handle 124, the left support bar 108, the right support bar 110, the curved chin bar 118, the chin rest 116, the left handle 112, the right handle 114, the head rest 122 and the handle 124. Moreover, this embodiment includes an adjustment bar 128 which elevates the chin rest 116 as desired by the eye professional/technician and/or the patient. However, this embodiment shows the bottom of the right 112 and the left 114 handles illustrating attachment configurations that stabilize the support system 100 to a table and eye testing device (both not shown).

Figure 11:
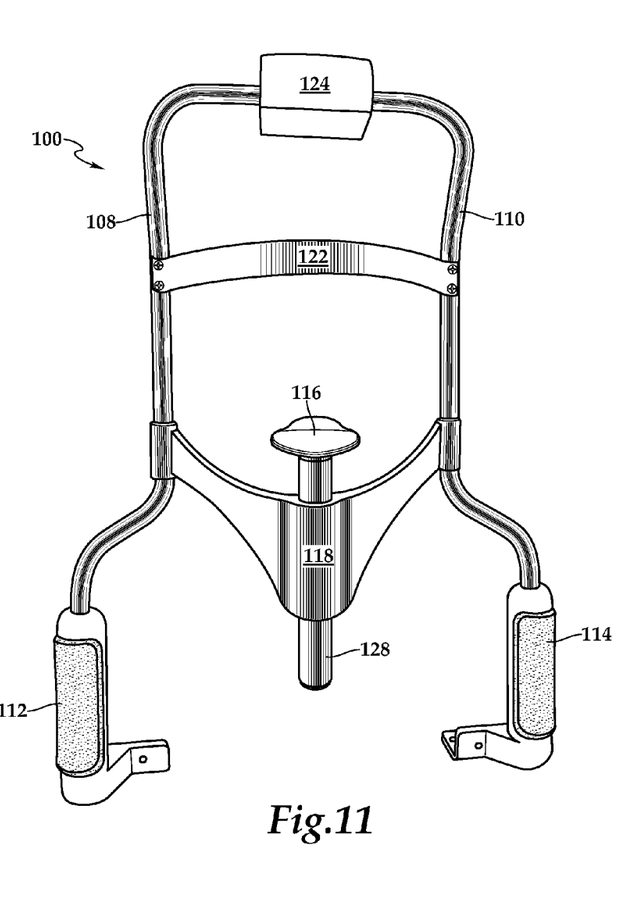
FIG. 11 illustrates a rear view of this embodiment of present invention.

FIG. 11 illustrates a rear view of an embodiment of the invention similar to the previously described embodiment. In this embodiment, the support system 100 includes the handle 124, the left support bar 108, the right support bar 110, the curved chin bar 118, the chin rest 116, the left handle 112, the right handle 114, the head rest 122 and the handle 124. Furthermore, this embodiment includes an adjustment bar 128 which elevates the chin rest 116 as desired by the eye professional/technician and/or the patient. However, this embodiment shows the bottom of the right 112 and the left 114 handles illustrating attachment configurations that stabilize the support system 100 to a table and eye testing device (both not shown).

Figure 12:
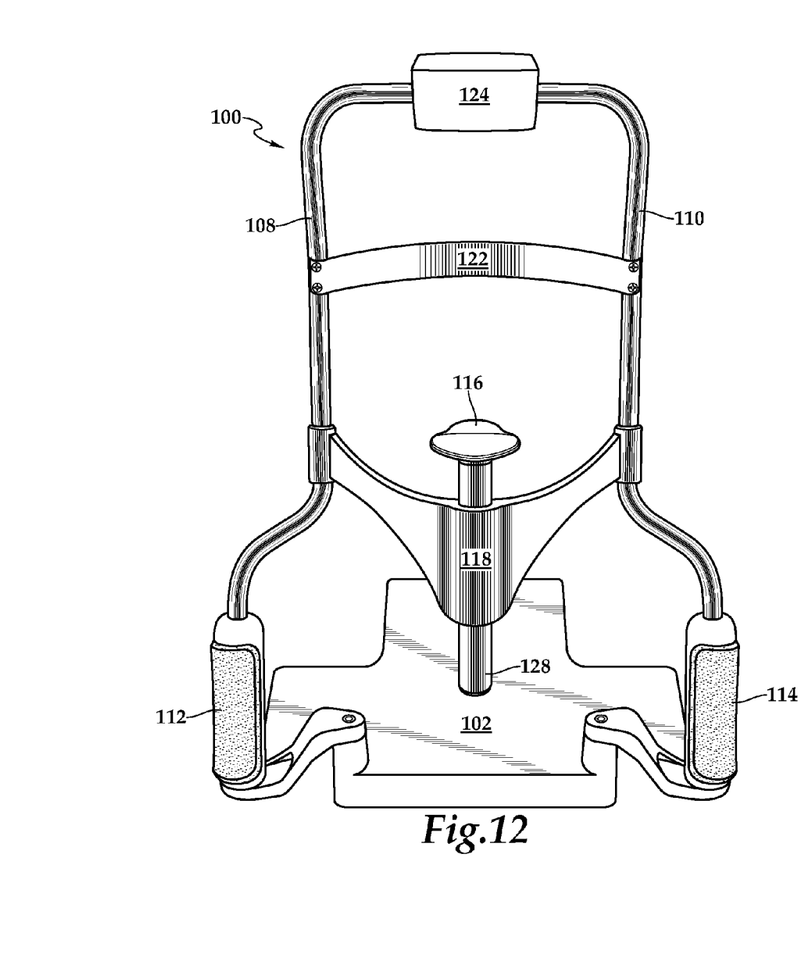
FIGS. 12-13 illustrate other front views of this embodiment of present invention.

FIG. 12 illustrates a front/top perspective of this embodiment of the invention. In this figure, the support system 100 includes the left support bar 108, the right support bar 110, the curved chin bar 118, the chin rest 116, the left handle 112, the right handle 114, the head rest 122 and the handle 124. However in this figure, the support system 100 is shown attached to table 102. Further, this embodiment includes an adjustment bar 128 which elevates the chin rest 116 as desired by the eye professional/technician and/or the patient.

Figure 13:
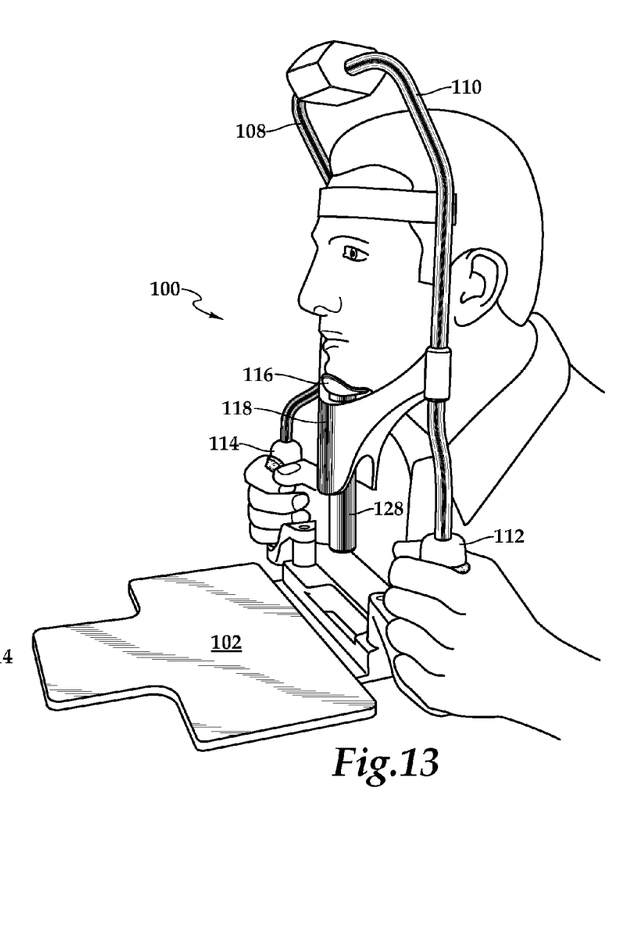

FIG. 13 shows the support system of FIG. 12 with a patient with his chin positioned in the chin rest as well as his forehead resting on the head rest in preparation to have his eyes examined by an eye professional/technician.

Figure 14:
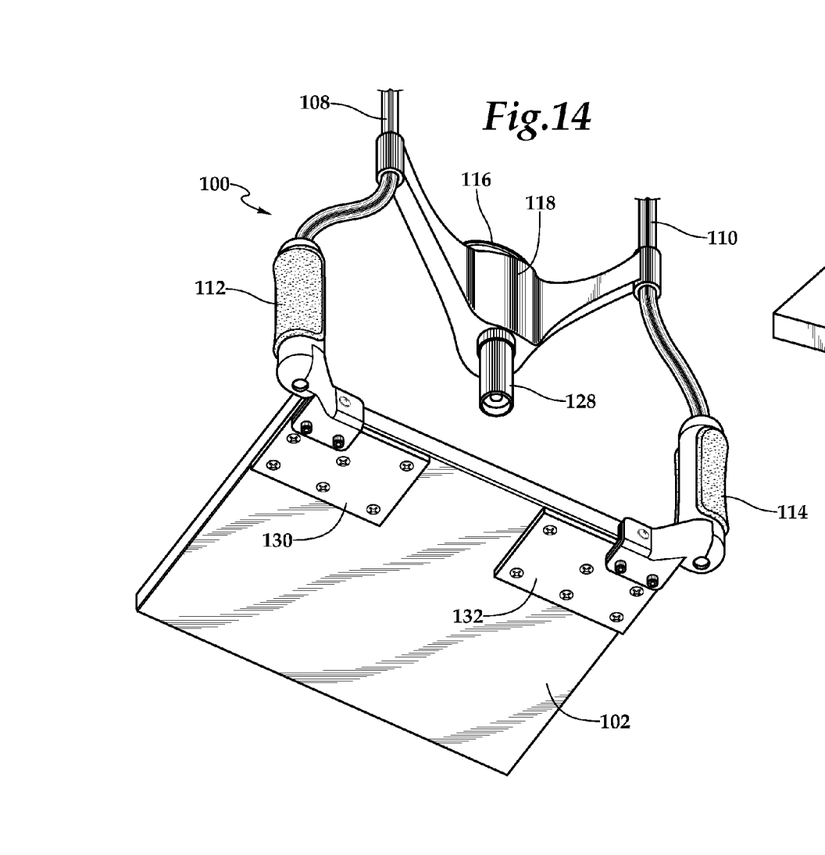
FIGS. 14-15 illustrate detailed view of the embodiment of the present invention.

FIG. 14 illustrates a support system 100 with the left support bar 108 and the left handle 112 along with the right support bar 110 and the right handle 114 attached to the table 102. The right 114 and left 112 handles are attached the right 132 and left 130 attachment plates that are used to secure the support system 100 to a table 102.

Figure 15:
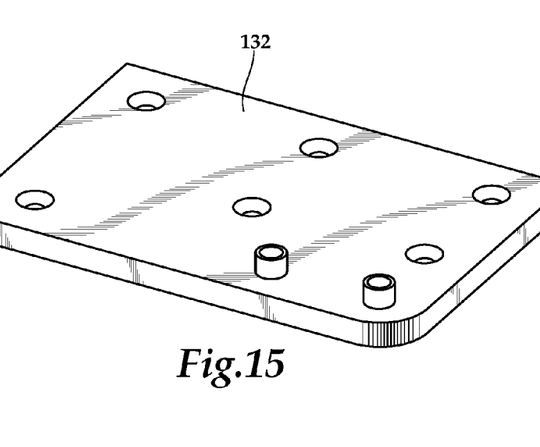

FIG. 15 illustrates a closer view of the right attachment plate 132 with a sample configuration that can be used to attach the right support bar 110 to the table 102.

Although this invention has been described with reference to an illustrative embodiment, this description is not intended to limit the scope of the invention. Various modifications and combinations of the illustrative embodiments as well as other embodiments of the invention will be apparent to persons skilled in the art upon reference to the description. It is therefore intended that the appended claims accomplish any such modifications or embodiments.

I claim:

1. An eye examination support device attached to an examination table, comprising:
    at least two support bars with handles and attachments at a bottom portion of each of the at least two support bars, wherein the at least two support bars are joined together at a top portion of the at least two support bars;
    a curved head rest attached to the at least two support bars;
    a curved chin rest bar attached to the at least two support bars;
    an adjustable chin rest attached on the curved chin rest bar;
    at least two attachment areas at a bottom of the each of the at least two support bars, wherein the at least two attachment areas attach each of the support bars to the examination table; and
    an examination device positioned near the adjustable chin rest and the curved chin rest bar in order to allow an eye professional and/or technician to examine at least one eye of a patient.

2. The support device of claim 1, wherein the adjustable chin rest adjusts vertically.

3. The support device of claim 1, wherein the adjustable chin rest is attached to the curved chin bar by an adjustment device to adjusts the adjustable chin rest vertically.

4. The support device of claim 1, wherein the curved chin bar is attached to one of the at least two support bars with an adjustment mechanisms that adjusts the curved chin bar vertically.

5. The support device of claim 1, wherein the examination device is attached to the support table.

6. The support device of claim 1, wherein the handles on each of the support bars include a winged area that attaches the support table.

7. The support device of claim 1 wherein the handles attach to a support level and the support table, and wherein the examination device is attached to the support level.

8. An eye examination support device attached to an examination table, comprising:
    two support bar with handles and attachments at a bottom portion of each of the two support bars, wherein the at least two support bars are joined together at a top portion of the at least two support bars;
    a curved head rest attached to the two support bars;
    a curved chin rest bar attached to the two support bars;
    an adjustable chin rest attached on the curved chin rest bar;
    two attachment areas at a bottom of the each of the two support bars, wherein the at least two attachment areas attach each of the support bars to the examination table; and
    an examination device positioned near the adjustable chin rest and the curved chin bar in order to allow an eye professional and/or technician to examine at least one eye of a patient.

9. The support device of claim 8, wherein the adjustable chin rest adjusts vertically.

10. The support device of claim 8, wherein the adjustable chin rest is attached to the curved chin bar by an adjustment device to adjusts the adjustable chin rest vertically.

11. The support device of claim 8, wherein the curved chin bar is attached to one of the at least two support bars with an adjustment mechanisms that adjusts the curved chin bar vertically.

12. The support device of claim 8, wherein the examination device is attached to the support table.

13. The support device of claim 8, wherein the handles on each of the support bars include a winged area that attaches the support table.

14. The support device of claim 8, wherein the handles attach to a support level and the support table, and wherein the examination device is attached to the support level.

15. An eye examination support device attached to an examination table, comprising:
    two support bar with attachments at a bottom portion of each of the two support bars;
    a curved head rest attached to the two support bars;
    an adjustable chin rest on a curved chin bar attached to the two support bars;
    two handles near a bottom of the each of the two support bars, wherein the two handles include an attachment area that attach each of the support bars to the examination table; and
    an examination device positioned near the adjustable chin rest and the curved chin bar in order to allow an eye professional and/or technician to examine at least one eye of a patient.

16. The support device of claim 15, wherein the examination table is free standing from any adjacent wall.

17. The support device of claim 15, wherein the examination table includes a power source attachment.

18. The support device of claim 17, wherein the power source connects the support device.

* * * * *